United States Patent
Kohara

(10) Patent No.: US 9,430,855 B2
(45) Date of Patent: Aug. 30, 2016

(54) X-RAY CT APPARATUS AND OPTIMAL CARDIAC PHASE DETERMINING METHOD

(75) Inventor: Ryota Kohara, Tokyo (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 241 days.

(21) Appl. No.: 14/122,376

(22) PCT Filed: Jun. 19, 2012

(86) PCT No.: PCT/JP2012/065557
§ 371 (c)(1),
(2), (4) Date: Nov. 26, 2013

(87) PCT Pub. No.: WO2012/176745
PCT Pub. Date: Dec. 27, 2012

(65) Prior Publication Data
US 2014/0192951 A1    Jul. 10, 2014

(30) Foreign Application Priority Data
Jun. 20, 2011  (JP) ................. 2011-135955

(51) Int. Cl.
*A61B 6/00* (2006.01)
*G06T 11/00* (2006.01)
(Continued)

(52) U.S. Cl.
CPC .......... *G06T 11/005* (2013.01); *A61B 5/0456* (2013.01); *A61B 6/032* (2013.01); *A61B 6/4078* (2013.01); *A61B 6/4233* (2013.01); *A61B 6/503* (2013.01); *A61B 6/5205* (2013.01); *A61B 6/5288* (2013.01); *G06T 2211/412* (2013.01)

(58) Field of Classification Search
USPC ................................ 378/4, 8, 901
See application file for complete search history.

(56) References Cited

U.S. PATENT DOCUMENTS

2002/0131545 A1* 9/2002 Hsieh .................. A61B 6/032
                                                        378/4
2004/0116804 A1* 6/2004 Mostafavi ............ A61B 5/743
                                                        600/428

(Continued)

FOREIGN PATENT DOCUMENTS

JP  2002-355241  12/2002
JP  2003-204961   7/2003

(Continued)

OTHER PUBLICATIONS

International Search Resort in PCT/JP2012/065557.

*Primary Examiner* — Phillip A Johnston
*Assistant Examiner* — Hsien Tsai
(74) *Attorney, Agent, or Firm* — Cooper & Dunham LLP

(57) ABSTRACT

In order to provide an X-ray CT apparatus and the like that can specify an optimal cardiac phase in a wide variety of cases, an X-ray CT apparatus collects X-ray information and electrocardiographic waveform data 5 by performing cardiac scanning using an scanning unit 1 (step S11). Then, reconstructed images of a plurality of cardiac phases are created (step S12), and a region-of-interest image is generated by extracting a region of interest for each of the reconstructed images of the plurality of cardiac phases (step S13). Then, a variation distribution image is generated by calculating a variation for each region-of-interest image (step S14). Then, the degree of harmony of each cardiac phase is calculated using the variation distribution image (step S15). Then, an optimal cardiac phase is determined on the basis of at least the degree of harmony (step S16).

12 Claims, 14 Drawing Sheets

(51) Int. Cl.
    *A61B 6/03*     (2006.01)
    *A61B 5/0456*     (2006.01)

(56) References Cited

U.S. PATENT DOCUMENTS

2004/0120450 A1*   6/2004   Flohr .................. A61B 5/0452
    378/4

2005/0129176 A1   6/2005   Kokubun et al.
2008/0128626 A1*   6/2008   Rousso .................. A61B 5/418
    250/362

FOREIGN PATENT DOCUMENTS

| | | |
|---|---|---|
| JP | 2004-121840 | 4/2004 |
| JP | 2008-6211 | 1/2008 |
| JP | 2009-28111 | 2/2009 |

* cited by examiner

X-RAY CT APPARATUS AND OPTIMAL CARDIAC PHASE DETERMINING METHOD

TECHNICAL FIELD

The present invention relates to an X-ray CT apparatus and the like to obtain a diagnostic image by irradiating an object with X-rays and in particular, to an X-ray CT apparatus and the like to determine an optimal cardiac phase in image reconstruction in cardiac scanning.

BACKGROUND ART

In cardiac scanning of the X-ray CT apparatus, in order to obtain a diagnostic image, a cardiac phase in which the motion of the heart is the slowest needs to be timely imaged. In recent years, scanning speed has been improved due to an increase in the rotation speed of the X-ray CT apparatus, an increase in the number of detectors arranged in rows, and the like. However, since the cross-sectional position of the coronary artery of the heart moves about 5 mm to 10 mm in 0.1 second, it is difficult to obtain a clear image without an afterimage even in the current situation. Therefore, it is necessary to create a diagnostic image by collecting the data of the heart rhythm in all cardiac phases and determining an optimal cardiac phase with slowest rhythm by data analysis.

As a technique of determining such an optimal cardiac phase, PTL 1 discloses a method of calculating the variation in the entire heart or a specific location using the data of adjacent cardiac phases and determining a cardiac phase with least motion as an optimal cardiac phase.

CITATION LIST

Patent Literature

[PTL 1] JP-A-2003-204961

SUMMARY OF INVENTION

Technical Problem

However, it is known that the heart rhythm differs depending on a location (for example, the right coronary artery and the left coronary artery). For this reason, in the method disclosed in PTL 1, a large motion occurred locally even in a cardiac phase in which it is estimated that the entire heart moves the slowest. In addition, in some cases, there has been a case where the motion of the entire heart or the motion of a local region other than the region of interest is large in a cardiac phase in which it is estimated that the local region of interest moves the slowest. In addition, in the method disclosed in PTL 1, there has been a case where it is difficult to specify the optimal cardiac phase since the rhythm of each region of the heart being significantly different is not taken into consideration. In particular, it has been difficult to specify the optimal cardiac phase for the rhythm of the unhealthy heart.

The present invention has been made in view of the above-described problems, and it is an object of the present invention to provide an X-ray CT apparatus and the like that can specify an optimal cardiac phase in a wide variety of cases.

Solution to Problem

In order to achieve the above-described object, a first invention is an X-ray CT apparatus including an X-ray irradiation unit that irradiates X-rays from periphery of an object, an X-ray detection unit that detects information of X-rays transmitted through the object, an electrocardiographic information acquisition unit that acquires electrocardiographic information of the object, an image creation unit that creates an image of the object from the X-ray information and the electrocardiographic information, and a display unit that displays the image. The X-ray CT apparatus includes: a tomographic data creation unit that creates a plurality of pieces of tomographic data with different cardiac phases from the X-ray information and the electrocardiographic information; a region data generation unit that generates region data by extracting a predetermined region for each piece of the tomographic data; a variation distribution calculation unit that calculates a variation distribution within the tomographic data by calculating a variation between cardiac phases regarding the region data; and a degree-of-harmony calculation unit that calculates a degree of harmony, which is an index indicating whether or not rhythms at respective locations of a target portion of the object are in harmony with each other, on the basis of the variation distribution.

A second invention is an optimal cardiac phase determining method in an X-ray CT apparatus including an X-ray irradiation unit that irradiates X-rays from periphery of an object, an X-ray detection unit that detects information of X-rays transmitted through the object, an electrocardiographic information acquisition unit that acquires electrocardiographic information of the object, an image creation unit that creates an image of the object from the X-ray information and the electrocardiographic information, and a display unit that displays the image. The optimal cardiac phase determining method includes: creating a plurality of pieces of tomographic data with different cardiac phases from the X-ray information and the electrocardiographic information; generating region data by extracting a predetermined region for each piece of the tomographic data, calculating a variation distribution within the tomographic data by calculating a variation between cardiac phases regarding the region data; and calculating a degree of harmony, which is an index indicating whether or not rhythms at respective locations of a target portion of the object are in harmony with each other, on the basis of the variation distribution.

Advantageous Effects of Invention

According to the present invention, it is possible to provide an X-ray CT apparatus and the like capable of specifying the optimal cardiac phase in a wide variety of cases.

DESCRIPTION OF EMBODIMENTS

Hereinafter, embodiments of the present invention will be described in detail with reference to the drawings.

First, referring to FIGS. 1 and 2, the configuration of an X-ray CT apparatus according to all embodiments will be described.

Figure 1:
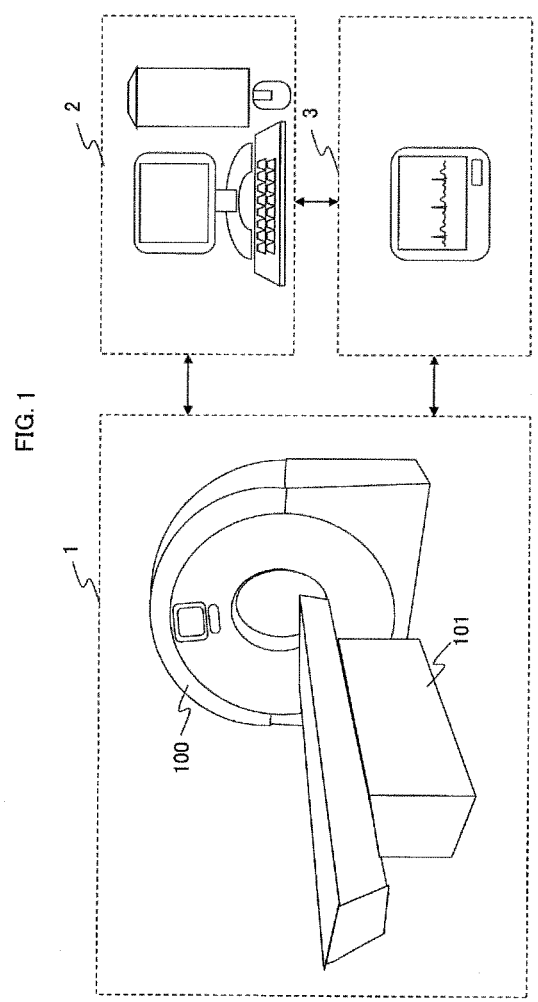
FIG. 1 is a diagram showing the overall configuration of an X-ray CT apparatus.

As shown in FIG. 1, the X-ray CT apparatus is configured to include an scanning unit 1, an operating unit 2, and an electrocardiograph 3, and the like. The scanning unit 1 includes a gantry 100 having a scanner body thereinside and a bed 101. The operating unit 2 operates and controls the scanning unit 1. In addition, the operating unit 2 performs input of the scanning conditions, image processing, and the like. The electrocardiograph 3 acquires the electrocardiographic waveform of an object 4.

Figure 2:
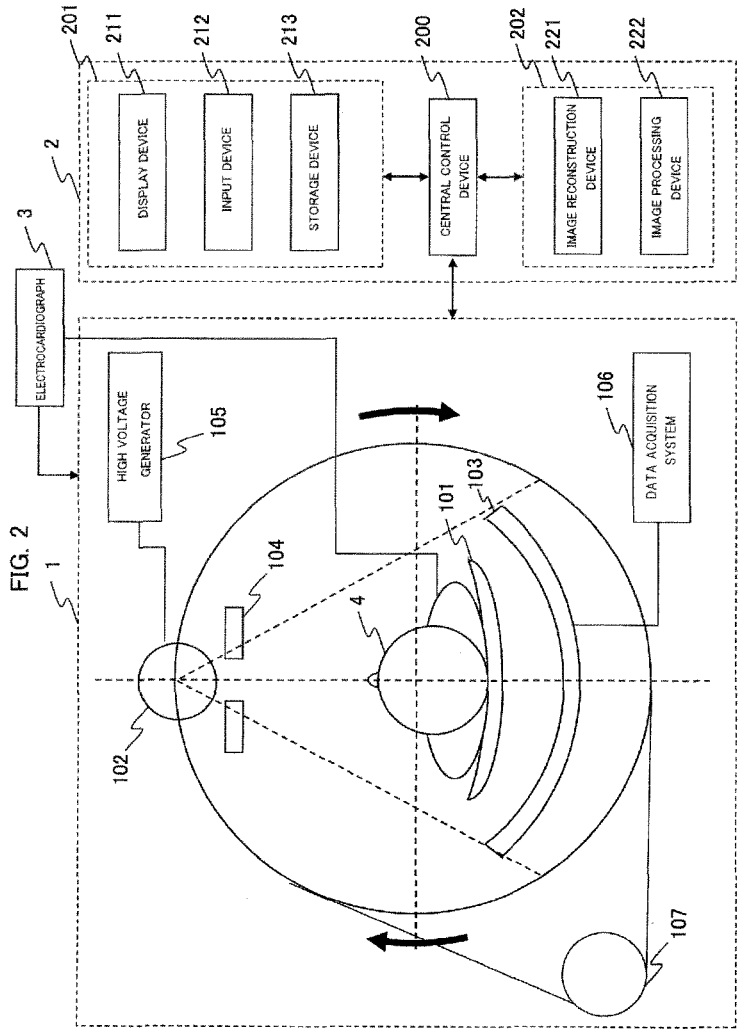
FIG. 2 is a diagram showing components of the X-ray CT apparatus.
Figure 3:
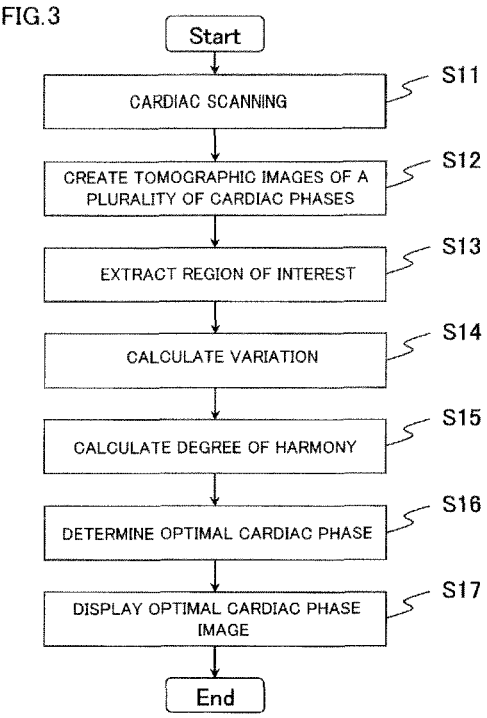
FIG. 3 is a flow chart showing an optimal cardiac phase determining process in a first embodiment.

As shown in FIG. 2, the gantry 100 is configured to include an X-ray generator 102 that irradiates X-rays from the periphery of the object 4, a collimator device 104 that narrows the range of the X-ray flux generated from the X-ray generator 102, an X-ray detector 103 that detects X-rays transmitted through the object 4, a high voltage generator 105 that applies a high voltage to the X-ray generator 102, a data acquisition system 106 that collects data detected by the X-ray detector 103, a driving device 107 that rotates a scanner around the object 4, and the like. In addition, the data acquisition system 106 also collects electrocardiographic information from the electrocardiograph 3 simultaneously.

The operating unit 2 is configured to include an input/output device 201, a calculation device 202, a central control device 200, and the like.

The input/output device 201 is configured to include a display device 211 that displays data such as an image, an input device 212 used when an operator inputs scanning conditions and the like, a storage device 213 that stores data required for scanning, such as a program and a device parameter, and the like.

The calculation device 202 is configured to include an image reconstruction device 221 that creates a reconstructed image of the object 4 on the basis of the data obtained from the scanning unit 1, an image processing device 222 that performs analysis of image data, and the like.

The central control device 200 controls each device of the scanning unit 1 and the operating unit 2 according to an operation instruction from the operator.

As scanning using an X-ray CT apparatus, there are rotation scanning in which scanning is performed while the X-ray generator 102 and the data acquisition system 106 are rotating within the gantry 100 and stationary scanning in which scanning is performed in a state where the X-ray generator 102 and the data acquisition system 106 stand still within the gantry 100. Tomographic scanning for obtaining a tomographic image of the object 4 is based on the rotation scanning. In addition, scanogram imaging for determining the scanning position of the tomographic scanning is based on the stationary scanning. In addition, the scanning trajectory of the tomographic scanning may be any of a circular trajectory, a spiral trajectory, and a combination of a circular trajectory and a spiral trajectory, and is not particularly limited.

The X-ray CT apparatus creates and displays an image of the object 4 on the basis of the X-ray information of the object 4 detected by the scanning unit 1 and the electrocardiographic information of the object 4 acquired by the electrocardiograph 3. In particular, the X-ray CT apparatus creates and displays an image of the object 4 by collecting the data of all cardiac phases and determining the optimal cardiac phase with the slowest heart rhythm by data analysis.

[First embodiment]

Hereinafter, a first embodiment will be described with reference to FIGS. 3 to 9. In particular, the flow of the optimal cardiac phase determining process in the first embodiment will be described with reference to FIG. 3, and details of each process will be described while appropriately referring to other diagrams. Hereinafter, a case where an image is used as tomographic data will be described. In addition, it is possible to achieve the object of the present invention by the same processing even if a sinogram is used as tomographic data. The sinogram is obtained by arranging projection data in order for each projection angle, and the horizontal axis indicates the position of the X-ray detector 103 and the vertical axis indicates the projection angle.

Hereinafter, it is assumed that "images" include not only an image, which is displayed on the display device 211 to be visualized, but also an image, which is stored in an internal memory of the calculation device 202 as a group of pixel values.

<Step S11: Cardiac Scanning>

First, a waveform collection portion of the electrocardiograph 3 is attached to the object 4, so that electrocardiographic information can be collected. Then, a contrast agent is administered to perform cardiac scanning using the scanning unit 1, thereby collecting transmitted X-ray data (X-ray information) and electrocardiographic waveform data 5 (electrocardiographic information: refer to FIG. 4). In addition, a contrast agent may not be administered depending on the scanning purposes.

Figure 4:
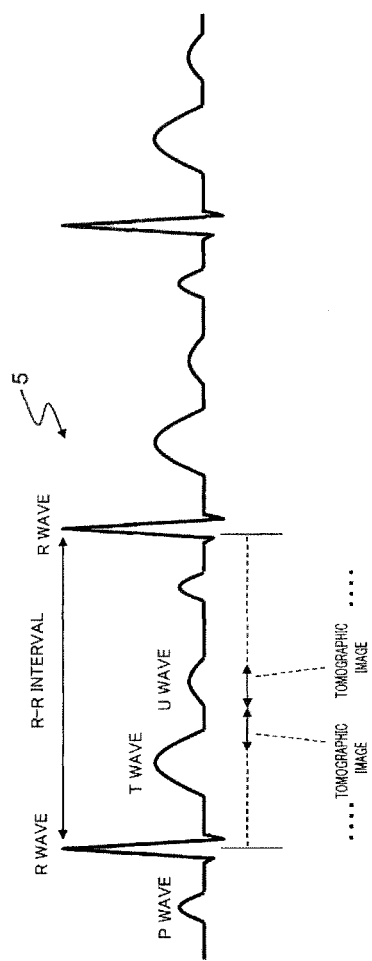
FIG. 4 is a diagram showing an example of electrocardiographic waveform data.

FIG. 4 shows the typical electrocardiographic waveform data 5 obtained by the electrocardiograph 3. The electrocardiographic waveform is a periodic waveform according to the heart rhythm. When creating images of a plurality of cardiac phases, a relative method may be used or an absolute method may be used as a method of expressing the time phase of the heart (cardiac phase). As the relative method, there is a method of expressing the relative position of the time phase as a percentage with an R-R interval as a reference.

As the absolute method, there is a method of expressing the time phase before and after an R wave as a time with the position of the R wave as a reference.

<Step S12: Creation of Tomographic Images of a Plurality of Cardiac Phases>

The image reconstruction device 221 reconstructs an image in each cardiac phase using transmitted X-ray data, thereby creating reconstructed images of a plurality of cardiac phases. Here, a plurality of cardiac phases are assumed to be included in the single R-R interval.

<Step S13: Extraction of a Region of Interest>

Figure 5:
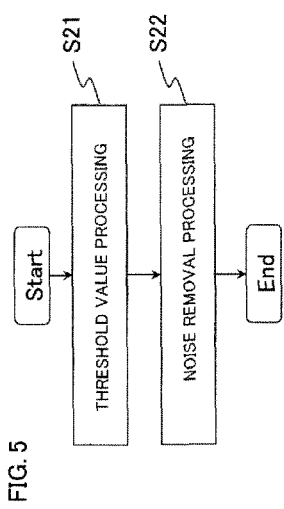
FIG. 5 is a flow chart showing a process of extracting a region of interest.

The image processing device 222 extracts a region of interest (contrast region or the like) on the basis of image information for each reconstructed image of the plurality of cardiac phases. FIG. 5 shows the details of a process of extracting the region of interest.

As shown in FIG. 5, first, the image processing device 222 extracts a candidate region of interest by replacing the pixel value of a pixel, which has a CT value equal to or less than a threshold value, with the threshold value by threshold value processing (step S21).

Then, the image processing device 222 extracts a region of interest as a region-of-interest image by removing a noise region, such as an isolated pixel (pixel whose surrounding pixels do not have pixel values) or a small region (small region compared with the area of the region of interest), from the candidate region of interest by noise removal processing (step S22).

<Step S14: Calculation of a Variation>

Figure 6:
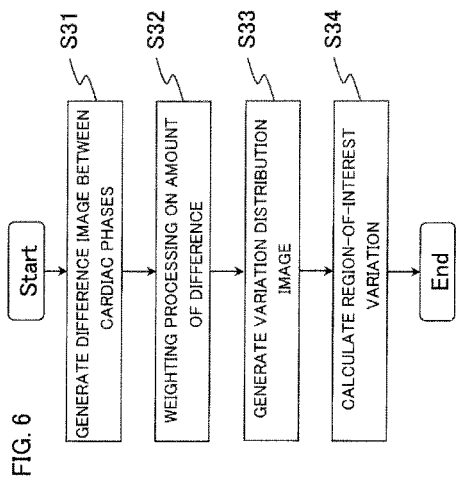
FIG. 6 is a flow chart showing a variation calculation process.

The image processing device 222 calculates a variation for each region-of-interest image of the plurality of cardiac phases. FIG. 6 shows the details of a process of calculating the variation.

As shown in FIG. 6, first, the image processing device 222 generates a difference image between cardiac phases by taking the amount of difference of each pixel for region extraction images of adjacent cardiac phases (step S31). The amount of difference may be a difference value including a negative value (a previous cardiac phase and a later cardiac phase are distinguished), or may be a positive value, such as an absolute value or a square value of the difference value. For example, assuming that the pixel value of the previous cardiac phase is $p_i$ and the pixel value of the later cardiac phase is $p_j$, the amount of difference may be any of $(p_j-p_i)$, $|p_j-p_i|$, and $(p_j-p_i)^2$. In the following explanation, the amount of difference is assumed to be a positive value in order to make the explanation easily understood.

Then, the image processing device 222 performs weighting processing on the amount of difference (step S32). In the weighting processing on the amount of difference, weighting is performed separately for a case where the target pixel itself moves in a different image between cardiac phases and a case where a peripheral pixel of the target pixel moves.

For example, it is assumed that the pixel position of a target pixel is (x, y) and the pixel position of a peripheral pixel of the target pixel is (x', y') (where x'≠x and y'≠y).

The case where the target pixel itself moves is a case where (x, y) in the region-of-interest image of the previous cardiac phase moves to (x', y') in the region-of-interest image of the later cardiac phase.

In addition, the case where the peripheral pixel moves is a case where (x', y') in the region-of-interest image of the previous cardiac phase moves to (x, y) in the region-of-interest image of the later cardiac phase.

Hereinafter, variation calculation processing according to variation factors in step S32 will be described in detail.

First, the image processing device 222 labels a pixel, which has an amount of difference equal to or greater than the threshold value, in a difference image between cardiac phases. Here, the threshold value may be a value (static value) set in advance in consideration of the extraction accuracy of the region of interest or an organ and tissue to which focus is given, or may be a value (dynamic value) based on the distribution of the amount of difference in a difference image between cardiac phases generated in step S31.

Then, the image processing device 222 determines the labeled pixel as a target pixel one by one, and performs iteration processing to be described later. In addition, the following processing may be performed not only using a single pixel as a target pixel but also using a plurality of pixels collectively as a target region.

In the iteration processing, the image processing device 222 gives a weighting to the difference between the target pixel and the labeled peripheral pixel (for example, a pixel closest to the target pixel) or the inter-pixel distance difference between the target pixel and the peripheral pixel, and calculates the result as a variation. In addition, the following processing may be performed not only using a single pixel as a peripheral pixel but also using a plurality of pixels collectively as a peripheral region.

Specifically, the image processing device 222 increases a weighting (for example, makes a weighting larger than the reference value) as a difference between the amount of difference of the target pixel and the amount of difference of the peripheral pixel decreases and the inter-pixel distance between the target pixel and the peripheral pixel increases. This case is equivalent to the "case where the target pixel itself moves" described above.

On the other hand, the image processing device 222 decreases a weighting (for example, makes a weighting smaller than the reference value) as a difference between the amount of difference of the target pixel and the amount of difference of the peripheral pixel increases and the inter-pixel distance between the target pixel and the peripheral pixel decreases. This case is equivalent to the "case where the peripheral pixel moves" described above.

Here, although it is necessary to determine the reference value of the weighting, the reference value of the weighting may be a static value or may be a dynamic value similarly to the threshold value of the labeling described above.

In addition, for a pixel that is not labeled, the image processing device 222 may calculate a lower variation than for a labeled pixel without considering the amount of difference of the peripheral pixel or the inter-pixel distance between the target pixel and the peripheral pixel, or may not calculate a variation assuming that there has been no variation.

In addition, in the variation calculation processing according to variation factors, it is not necessary to accurately determine whether the target pixel has moved or the peripheral pixel has moved. First of all, it is not possible to accurately determine in which direction and by which amount each cell of the object 4 has moved. In addition, in view of the purpose of the present invention, there is no problem even if the accuracy of the variation calculation processing according to variation factors is slightly low.

Figure 9:
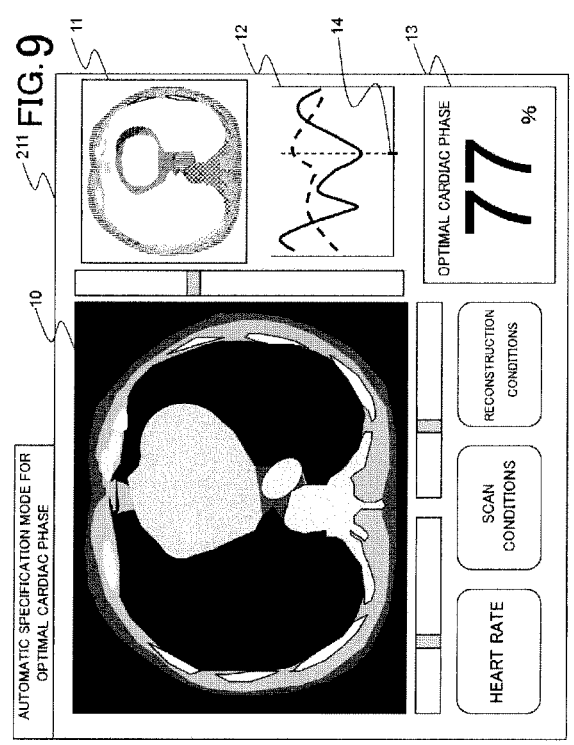
FIG. 9 is a schematic diagram of a screen that displays an optimal cardiac phase image.

Then, the image processing device 222 generates a variation distribution image indicating the distribution of the variation calculated in S32 (step S33). FIG. 9 shows an example of a variation distribution image 11. Details of FIG. 9 will be described later.

Then, the image processing device 222 calculates the sum of the variation of the entire region of interest as a region-of-interest variation on the basis of the variation distribution image generated in S33 (step S34).

In addition, the region-of-interest variation may be a weighted average value in the region of interest or the like.

<Step S15: Calculation of the Degree of Harmony>

Figure 7:
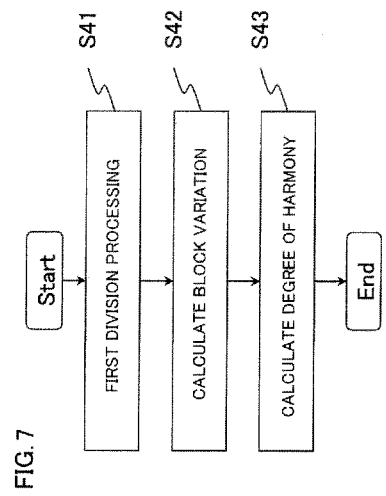
FIG. 7 is a flow chart showing a process of calculating the degree of harmony.

The image processing device 222 calculates the degree of harmony of each cardiac phase using a variation distribution image. FIG. 7 shows the details of a process of calculating the degree of harmony.

Here, the degree of harmony is an index indicating whether or not the rhythms at respective locations of a target portion (for example, the heart) of the object 4 are in harmony with each other. In order to conform to this meaning, the image processing device 222 calculates a high value of the degree of harmony relevant to the cardiac phase when individual pixels move similarly, and calculates a low value of the degree of harmony relevant to the cardiac phase when individual pixels move apart.

The present invention determines an optimal cardiac phase in consideration of not only the entire motion but also the local motion on the basis of the findings that (1) there is a place of large motion locally even in a cardiac phase estimated that the entire heart moves most slowly, (2) motion of the entire heart or motion of a local region other than a region of interest may be large in a cardiac phase estimated that a local region of interest moves most slowly, and (3) influence of these phenomena on diagnosis cannot be neglected especially for the rhythm of the unhealthy heart. That is, in the present invention, the optimal cardiac phase is determined using at least the degree of harmony described above.

As shown in FIG. 7, as first division processing, the image processing device 222 divides a region of interest into blocks according to the magnitude of variation in the variation distribution image (step S41). Here, the image processing device 222 divides a region of interest into several blocks on the basis of the threshold value of the static or dynamic value.

As a simplest example, the image processing device 222 divides a region of interest into two blocks of a region with a large variation and a region with a small variation.

Then, the image processing device 222 calculates a block variation of each block (step S42). The block variation may be any of the sum of variations of all pixels in a block, the weighted average value, and the maximum value.

Then, the image processing device 222 calculates the degree of harmony for each cardiac phase (step S43).

For example, the image processing device 222 calculates the degree of harmony H of a region of interest C using the following Expression.

$$H = \sum_{i \in C} a_i u_i \quad (1)$$

Here, $a_i$ is an amount relevant to the area of each block, and $u_i$ is an amount relevant to the variation of each block. It is preferable that $a_i$ be proportional to the area of a block, and it is preferable that $u_i$ be inversely proportional to the variation of a block. As a simplest example, H=S×t is satisfied assuming that S is the area of a region of interest and t is an inverse of a region-of-interest variation.

In addition, when calculating the degree of harmony, the image processing device 222 may set the reference area and the reference block variation to normalize or score a and u in advance. In addition, when calculating the degree of harmony, the image processing device 222 may perform weighting in consideration of the block shape for the area.

In addition, the image processing device 222 may calculate the degree of harmony H using Expressions (2) to (5) shown below as specific examples of Expression (1).

$$H = \sum_{i \in C} \frac{s_i}{t_i} \quad (2)$$

$$H = \frac{\max_{i \in C}(s_i)}{\sum_{i \in C} s_i} \quad (3)$$

$$H = \frac{s_{\arg\min_{i \in C}(t_i)}}{\sum_{i \in C} s_i} \quad (4)$$

$$H = \max_{i \in C}\left(\frac{s_i}{t_i}\right) \quad (5)$$

In Expressions (2) to (5), $S_i$ is the area of a block, and $t_i$ is a block variation.

Expression (2) is the sum of (area of a block/block variation).

Expression (3) is a maximum value of the area of a block/(sum of the areas of blocks).

Expression (4) is the area of a block having a minimum block variation/(sum of the areas of blocks).

Expression (5) is a maximum value of (area of a block/block variation).

In addition, in processing to be described later, the image processing device 222 may use the inverse of the degree of harmony or a difference of the degree of harmony from a predetermined value as a degree of in harmony. The following explanation will be given on the assumption that the image processing device 222 uses the degree of harmony.

Figure 8:
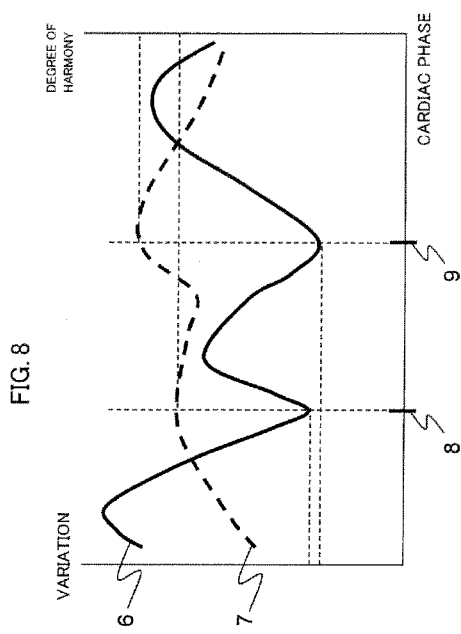
FIG. 8 is a schematic diagram of a graph of the variation and the degree of harmony.

FIG. 8 shows a region-of-interest variation graph 6 in a solid line and a degree-of-harmony graph 7 in a dashed line. FIG. 8 is a graph in which the cardiac phase is on the horizontal axis and the variation or the degree of harmony is on the vertical axis.

As can be seen from FIG. 8, the region-of-interest variation graph 6 has valleys (minimum values) in two places of cardiac phases 8 and 9. Since there is almost no difference between the region-of-interest variations of the cardiac phases 8 and 9, it is difficult to determine which of the cardiac phases 8 and 9 is to be selected as an optimal cardiac phase. In particular, in the case of a person having a heart disease (for example, a person with fast cardiac motion), a clear valley of the region-of-interest variation is not present, or the valley of the region-of-interest variation is present at a location different from a healthy person.

In contrast, when the degree-of-harmony graph 7 is viewed, the degree-of-harmony graph 7 has mountains (maximum values) in two places. Since a difference between the degree of harmony of the cardiac phase 8 and the degree of harmony of the cardiac phase 9 is clear, it can be determined that it is preferable to select the cardiac phase 9 as an optimal cardiac phase.

<Step S16: Optimal Cardiac Phase Determining Process>

The image processing device 222 determines an optimal cardiac phase on the basis of the variation or the degree of harmony. As a simplest example, the image processing device 222 determines a cardiac phase, in which the region-of-interest variation is small and the degree of harmony is large, as an optimal cardiac phase.

In addition, the processing of step S16 is not essential. For example, the image processing device 222 may display the graph shown in FIG. 8 on the display device 211, and the user may determine the optimal cardiac phase while referring to the graph displayed on the display device 211.

<Step S17: Display of an Optimal Cardiac Phase Image>

The image reconstruction device 221 generates an optimal cardiac phase image, which is a reconstructed image in the optimal cardiac phase, and displays it on the display device 211. FIG. 9 shows a display example of the optimal cardiac phase and the like.

In FIG. 9, an optimal cardiac phase image 10, a variation distribution image 11, a region-of-interest variation and degree-of-harmony graph 12, and an optimal cardiac phase 13 are schematically shown. In addition, the variation distribution image 11 shows places where the variations are different due to differences in the pattern or differences in shades of gray scale.

The optimal cardiac phase image 10 is generated in step S17. The variation distribution image is generated in step S33. The region-of-interest variation and degree-of-harmony graph 12 is the same as in FIG. 8. The optimal cardiac phase 13 is determined in step S16.

As described above, the optimal cardiac phase may be automatically determined by the image reconstruction device 221, or may be determined through the input device 212 by the user.

When the user determines the optimal cardiac phase, the optimal cardiac phase is determined by moving a linear slide 14, which is displayed on the region-of-interest variation and degree-of-harmony graph 12, to the position of the desired cardiac phase. In this case, the image reconstruction device 221 may follow the movement of the linear slide 14 to update the display of the optimal cardiac phase image 10, the variation distribution image 11, and the optimal cardiac phase 13.

As described above, the X-ray CT apparatus according to the first embodiment calculates the degree of harmony (index indicating whether or not the rhythms at respective locations of the heart are in harmony with each other) for each cardiac phase, and determines the optimal cardiac phase using the degree of harmony or displays the degree of harmony so that the user determines the optimal cardiac phase.

Thus, the X-ray CT apparatus according to the first embodiment can specify the cardiac phase, which is slow and in harmony, in consideration of the uniformity of the rhythm at each location of the heart. As a result, it is possible to provide an optimal diagnostic image. This will be described more specifically. In the related art, an image in which the total variation is minimal is selected as the optimal cardiac phase image (=diagnostic image). However, there has been a case where a diagnostic portion has an image quality, which is not suitable for diagnosis, since the uniformity of the rhythm at each location of the heart is not taken into consideration. On the other hand, since the X-ray CT apparatus according to the first embodiment determines the optimal cardiac phase on the basis of the degree of harmony, the uniformity of the rhythm at each location of the heart is taken into consideration. Therefore, in the first embodiment, the variation of the entire image may not be minimal, but there is no case where a diagnostic portion has an image quality unsuitable for diagnosis.

In addition, even if there is a plurality of time phases that has the same degree of variation, it is possible to determine the optimal cardiac phase. In addition, since a variation distribution image is displayed, a user can set reconstruction conditions (for example, weighting in a viewing direction) suitable for the variation.

In addition, although the case where the degree of harmony in tomographic data (two-dimensional region) is calculated has been described above, the application range of the present invention is not limited to the two-dimensional region, and can be extended to a three-dimensional region. In the case of a three-dimensional region, the X-ray CT apparatus calculates the variation and the degree of harmony in consideration of a variation in the axial direction of a plurality of cross-sections.

[Second embodiment]

The first embodiment is suitable for a case where the contrast ratio of a contrast region and a non-contrast region is high as in contrast scanning since the correlation of the variation in the entire region of interest is taken into consideration. In a second embodiment, a preferred form in cardiac scanning in which no contrast medium is administered will be described.

Processing of an X-ray CT apparatus according to the second embodiment is the same as that in the first embodiment except for the details (refer to FIG. 10) of processing of step S15, and repeated explanation thereof will be omitted. In the second embodiment, however, a region of interest is extracted on the basis of a CT value corresponding to a real portion instead of the CT value corresponding to the contrast region in step S13, and is set as a region-of-interest image.

Figure 10:
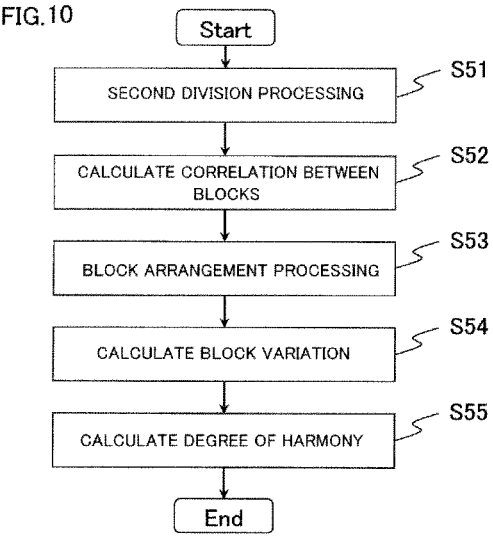
FIG. 10 is a flow chart showing a process of calculating the degree of harmony in a second embodiment.

Details of processing of step S15 in the second embodiment will be described with reference to FIG. 10.

As second division processing, the image processing device 222 divides a region-of-interest image mechanically (step S51). Here, the second division processing is division processing in which the magnitude of variation is not taken into consideration. In the second division processing, an overlapping region is allowed, and the region-of-interest image is divided into a plurality of blocks of three or more blocks. The shape of a block may be a circle or may be a rectangle. As a simplest example, the image processing device 222 divides a region-of-interest image into grid-like blocks.

In addition, the image processing device 222 calculates a provisional block variation for each block by the same processing as in the first embodiment.

Then, the image processing device 222 calculates a correlation coefficient of variation between blocks using the provisional block variation (step S52). In addition, any value may be used as long as it indicates the degree of association between blocks on the basis of the variation between blocks, without being limited to the correlation coefficient.

Then, as section arrangement processing, the image processing device 222 re-classifies blocks, which have a correlation coefficient equal to or greater than the threshold value, into the same block (step S53). The image processing device 222 continues the processing of re-classification, for example, until the number of blocks becomes 2 or less.

Then, the image processing device 222 calculates a block variation of each of arranged blocks by the same processing as in the first embodiment (step S54).

Then, the image processing device 222 calculates the degree of harmony in consideration of the block variation and the block area of each of the arranged blocks by the same processing as in the first embodiment (step S55).

Also in the second embodiment, the same effects as in the first embodiment are obtained. In addition, in the second embodiment, the region-of-interest image is mechanically divided into blocks. Accordingly, even if the contrast of a region of interest and a peripheral region is low as in cardiac scanning in which no contrast medium is used, it is possible to specify the slow and harmonious cardiac phase in consideration of the correlation of the motion within a cross-section of the heart.

[Third embodiment]

The first and second embodiments are suitable for a case where the scanning result is good. In a third embodiment, a case where contrast scanning is not good and contrast spots and the like cannot be neglected will be described. In addition, the third embodiment can also be applied to a case where the extraction of a contrast region is not good.

Processing of an X-ray CT apparatus according to the third embodiment is the same as that in the first embodiment except for the details (refer to FIG. 11) of processing of step S15, and repeated explanation thereof will be omitted. In the third embodiment, however, in step S13, a good contrast region and a poor contrast region including a region of contrast spots or a region of poor extraction are extracted, and a region-of-interest image in which the good contrast region and the poor contrast region are distinguished is generated.

Figure 11:
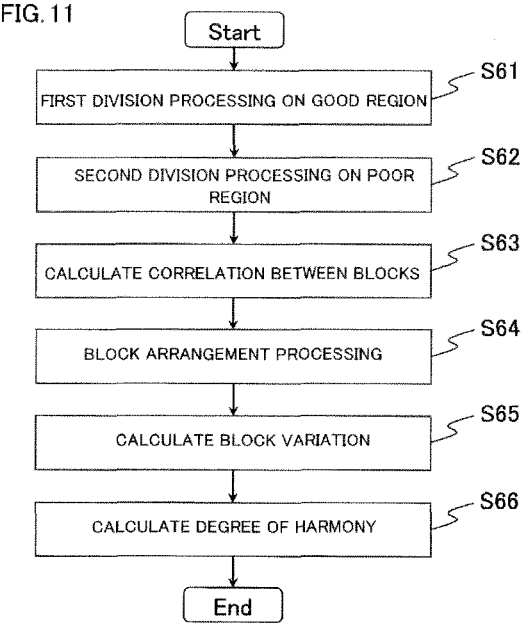
FIG. 11 is a flow chart showing a process of calculating the degree of harmony in a third embodiment.

Details of processing of step S15 in the third embodiment will be described with reference to FIG. 11.

The image processing device 222 performs first division processing on the good contrast region as in step S41 in the first embodiment (step S61).

Then, the image processing device 222 performs second division processing on the poor contrast region as in step S51 in the second embodiment (step S62).

Then, the image processing device 222 calculates a correlation coefficient of variation between a block of the good contrast region and a block of the poor contrast region (step S63).

Then, the image processing device 222 performs block arrangement by integrating a poor contrast block, which has a correlation coefficient equal to or greater than a threshold value, with a good contrast block (step S64).

Then, the image processing device 222 calculates the block area and the block variation after block arrangement (step S65).

Then, the image processing device 222 calculates the degree of harmony in consideration of the block area and the block variation after block arrangement by the same processing as in the first embodiment (step S66).

Also in the third embodiment, the same effects as in the first embodiment are obtained. In addition, in the third embodiment, processing suitable for each of the good contrast region and the poor contrast region is performed. Accordingly, even if a poor contrast region is included, the influence of motion depending on the position of the heart can be taken into consideration. As a result, it is possible to determine the cardiac phase that is slow and in harmony.

[Fourth embodiment]

In a fourth embodiment, details of the interface of an input and output screen will be described with reference to FIGS. 12 to 14. In the fourth embodiment, the threshold value of the division processing in step S41 of the first embodiment is changed to correct the division processing.

Figure 12:
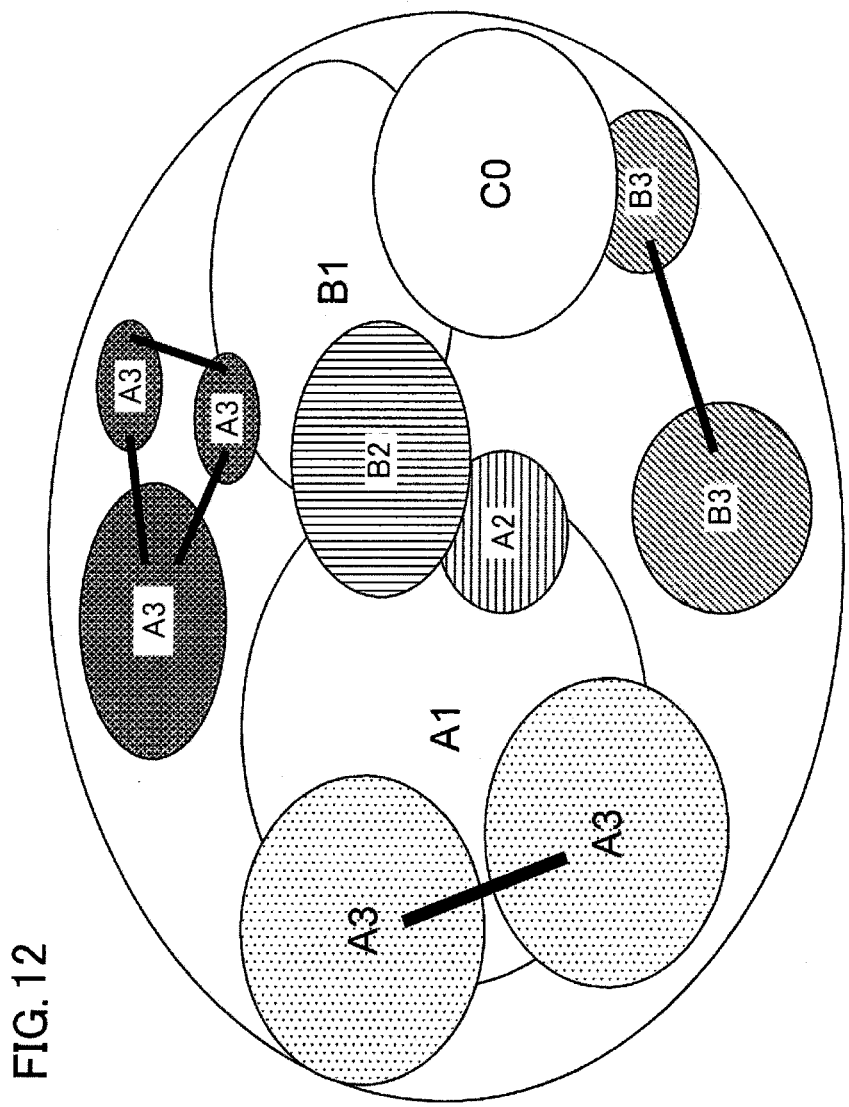
FIG. 12 is a schematic diagram of a screen for displaying the association between blocks.

FIG. 12 schematic shows a screen for displaying the association between blocks. In FIG. 12, ellipses having symbols, such as "A1" and "A2", thereinside show regions of respective blocks. In addition, a straight line (connecting line) connecting the ellipses is given to blocks that are integrated when the threshold value is increased by one step. In addition, the elliptical insides of the blocks that are integrated when the threshold value is increased by one step are shown by the same pattern.

The image processing device 222 displays the screen shown in FIG. 12 on the display device 211. The user determines whether or not to change the threshold value while referring to the screen shown in FIG. 12. When an instruction to change the threshold value is given, the image processing device 222 performs division processing on the basis of the changed threshold value.

Figure 13:
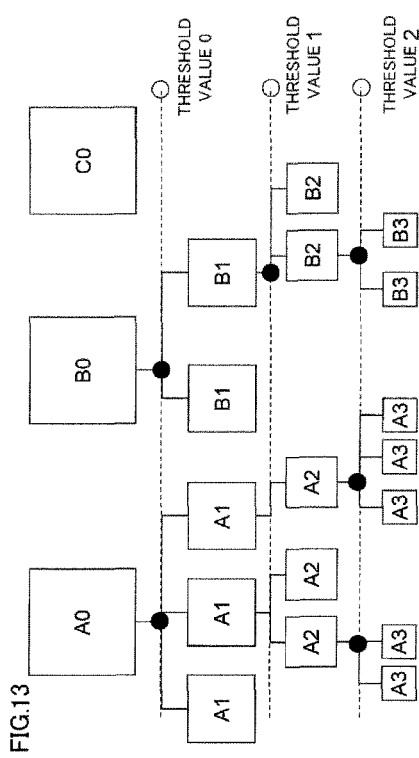
FIG. 13 is a schematic diagram of a screen for instructing the integration or separation of blocks by change in the threshold value.

FIG. 13 schematically shows a screen for instructing the integration or separation of blocks by the change in the threshold value. In FIG. 13, the association shown in FIG. 12 is expressed in a tree form. Rectangles having symbols, such as "A1" and "A2", thereinside show regions of respective blocks.

The user can fold up (not display) or expand (display) the tree below the target block by specifying the black circle through the input device 212.

In addition, the user can fold up (not display) or expand (display) the tree of lower order for each hierarchy by specifying the white circle through the input device 212.

Figure 14:
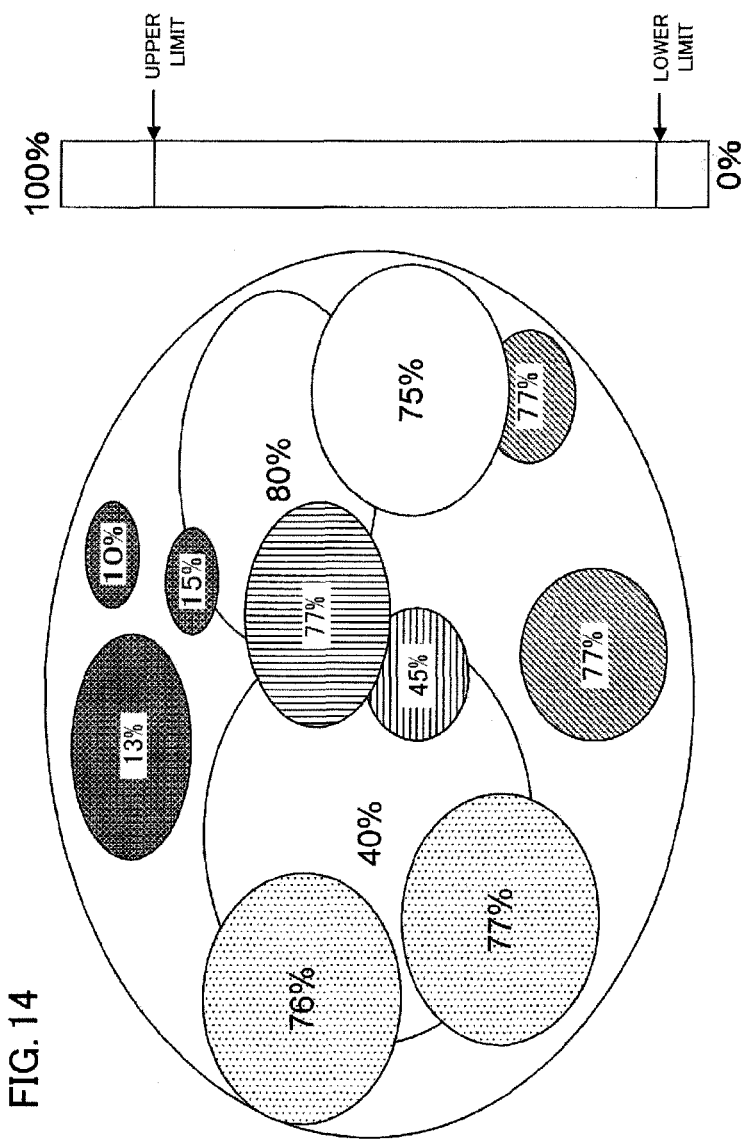
FIG. 14 is a schematic diagram of a screen for instructing the change in the display range by change in the upper and lower limits of the threshold value.

FIG. 14 schematically shows a screen for instructing the change the display range by changing the upper and lower limits of the threshold value. In FIG. 14, ellipses having numeric values, such as "13%" and "10%", thereinside show regions of respective blocks. The numeric value inside the ellipse indicates an optimal cardiac phase for each block calculated from only the variation. In addition, the elliptical insides of blocks that are highly associated with each other are shown by the same pattern.

The user can change the width of the cardiac phase to be displayed by moving the upper limit or the lower limit of a slide bar on the right side.

For example, when the lower limit is set to 30%, ellipses to which "10%", "13%", and "15%" are given are no longer displayed. In addition, for example, when the upper limit is set to 79%, an ellipse to which "80%" is given is no longer displayed.

According to the fourth embodiment, user operability is improved. As a result, it is possible to quickly specify the optimal cardiac phase.

While the preferred embodiments of the X-ray CT apparatus according to the present invention have been described with reference to the accompanying drawings, the present invention is not limited to such examples. It is apparent to those skilled in the art that various changes and modifications can be made within the range of the technical idea disclosed in this specification, and it should undoubtedly be understood that they also belong to the technical range of the present invention.

REFERENCE SIGNS LIST

1: scanning unit
2: operating unit
3: electrocardiograph
4: object
5: electrocardiographic waveform data
6: region-of-interest variation graph
7: degree-of-harmony graph
8, 9: cardiac phase
10: optimal cardiac phase image
11: variation distribution image
12: region-of-interest variation and degree-of-harmony graph
13: optimal cardiac phase
14: linear slide

The invention claimed is:

1. An X-ray CT apparatus, comprising:
   an X-ray irradiation unit that irradiates X-rays from periphery of an object;
   an X-ray detection unit that detects information of X-rays transmitted through the object;
   an electrocardiographic information acquisition unit that acquires electrocardiographic information of the object;
   an image creation unit that creates an image of the object from the X-ray information and the electrocardiographic information;
   a display unit that displays the image;
   a tomographic data creation unit that creates a plurality of pieces of tomographic data with different cardiac phases from the X-ray information and the electrocardiographic information;
   a region data generation unit that generates region data by extracting a predetermined region for each piece of the tomographic data;
   a variation distribution calculation unit that calculates a variation distribution within the tomographic data by calculating a variation between cardiac phases regarding the region data; and
   a degree-of-harmony calculation unit that calculates a degree of harmony, which is an index indicating whether local locations of a target portion of the object move similarly, on the basis of the variation distribution.

2. The X-ray CT apparatus according to claim 1,
   wherein the degree-of-harmony calculation unit divides the region data into a plurality of blocks on the basis of the variation distribution, and calculates the degree of harmony on the basis of an area of each of the blocks and the variation of each of the blocks.

3. The X-ray CT apparatus according to claim 1,
   wherein the variation distribution calculation unit calculates an amount of difference for the region data of adjacent cardiac phases, specifies a target region from a region having the amount of difference equal to or greater than a predetermined value, sets a region located around the target region, in the region having the amount of difference equal to or greater than the predetermined value, as a peripheral region, and calculates the variation by giving a weighting to the amount of difference of the target region on the basis of a difference between the amount of difference of the target region and the amount of difference of the peripheral region and an inter-region distance between the target region and the peripheral region.

4. The X-ray CT apparatus according to claim 1, further comprising:
   an optimal cardiac phase determination unit that determines an optimal cardiac phase from a plurality of cardiac phases using at least the degree of harmony.

5. The X-ray CT apparatus according to claim 2,
   wherein the degree-of-harmony calculation unit arranges the blocks, which are divided first, according to a degree of association between the blocks divided first.

6. The X-ray CT apparatus according to claim 2,
   wherein the degree-of-harmony calculation unit displays the blocks on the display unit according to a degree of association between the blocks divided first.

7. The X-ray CT apparatus according to claim 6,
   wherein the degree-of-harmony calculation unit displays blocks, which are highly associated with each other compared with a degree of association with other blocks, on the display unit by the same pattern.

8. The X-ray CT apparatus according to claim 6,
   wherein the degree-of-harmony calculation unit connects blocks, which are highly associated with each other compared with a degree of association with other blocks, to each other and displays a result on the display unit.

9. The X-ray CT apparatus according to claim 6,
   wherein the degree-of-harmony calculation unit displays the blocks on the display unit in a tree structure according to the degree of association.

10. An optimal cardiac phase determining method in an X-ray CT apparatus comprising an X-ray irradiation unit that irradiates X-rays from periphery of an object, an X-ray detection unit that detects information of X-rays transmitted through the object, an electrocardiographic information acquisition unit that acquires electrocardiographic information of the object, an image creation unit that creates an image of the object from the X-ray information and the electrocardiographic information, and a display unit that displays the image, the method including:
    (a) creating a plurality of pieces of tomographic data with different cardiac phases from the X-ray information and the electrocardiographic information;
    (b) generating region data by extracting a predetermined region for each piece of the tomographic data;
    (c) calculating a variation distribution within the tomographic data by calculating a variation between cardiac phases regarding the region data; and
    (d) calculating a degree of harmony, which is an index indicating whether local locations of a target portion of the object move similarly, on the basis of the variation distribution.

11. The optimal cardiac phase determining method according to claim 10,
    wherein in (d), the region data is divided into a plurality of blocks on the basis of the variation distribution, and the degree of harmony is calculated by employing one or more of the following expressions (2) to (5), to calculate the degree of harmony H of the region data C:

$$H = \sum_{i \in C} \frac{s_i}{t_i} \qquad (2)$$

$$H = \frac{\max_{i \in C}(s_i)}{\sum_{i \in C} s_i} \qquad (3)$$

$$H = \frac{S_{\arg\min_{i \in C}(t_i)}}{\sum_{i \in C} s_i} \qquad (4)$$

$$H = \max_{i \in C}\left(\frac{s_i}{t_i}\right), \qquad (5)$$

where $S_i$ is the area of block i, and $t_i$, is a block variation.

12. The X-ray CT apparatus according to claim 1, wherein the degree-of-harmony calculation unit divides the region data into a plurality of blocks on the basis of the variation distribution, and employs one or more of the following expressions (2) to (5), to calculate the degree of harmony H of the region data C:

$$H = \sum_{i \in C} \frac{s_i}{t_i} \qquad (2)$$

-continued $$H = \frac{\max_{i \in C}(s_i)}{\sum_{i \in C} s_i} \quad (3)$$

$$H = \frac{S_{\arg\min_{i \in C}(t_i)}}{\sum_{i \in C} s_i} \quad (4)$$

$$H = \max_{i \in C}\left(\frac{s_i}{t_i}\right), \quad (5)$$

where $S_i$, is the area of block i, and $t_i$, is a block variation.

* * * * *